United States Patent [19]

DeChellis et al.

[11] Patent Number: 4,921,486
[45] Date of Patent: May 1, 1990

[54] DISPOSABLE SYRINGE WITH RETRACTING NEEDLE

[76] Inventors: Francis M. DeChellis; Deborah K. DeChellis, both of 654 Bayou DuLarge Rd., Houma, La. 70363

[21] Appl. No.: 369,758
[22] Filed: Jun. 23, 1989
[51] Int. Cl.⁵ .............................................. A61M 5/00
[52] U.S. Cl. ..................................... 604/110; 604/195
[58] Field of Search ............... 604/110, 187, 192, 195, 604/198, 263

[56] References Cited

U.S. PATENT DOCUMENTS 4,795,432 1/1989 Karczmer .......................... 604/110

FOREIGN PATENT DOCUMENTS 2202747 10/1988 United Kingdom ................ 604/192

Primary Examiner—John D. Yasko
Attorney, Agent, or Firm—James M. Peppers

[57] ABSTRACT

A disposable hypodermic syringe adapted to be easily disabled against re-use or flesh pricking. Has an outer barrel, an inner reservoir body fitted within the barrel, a needle support member connected to the reservoir body, a hypodermic needle mounted in the support body, and an elastic member mounted in stressed condition between the needle support member and the barrel member for expanding and moving the needle into the barrel member when the elastic member is released. The reservoir body is separated from the needle support member by applying torque between the barrel member and the reservoir body to part a plurality of web linkages and permit the spring to expand and push the needle support member and hypodermic needle to within the reservoir body.

20 Claims, 2 Drawing Sheets

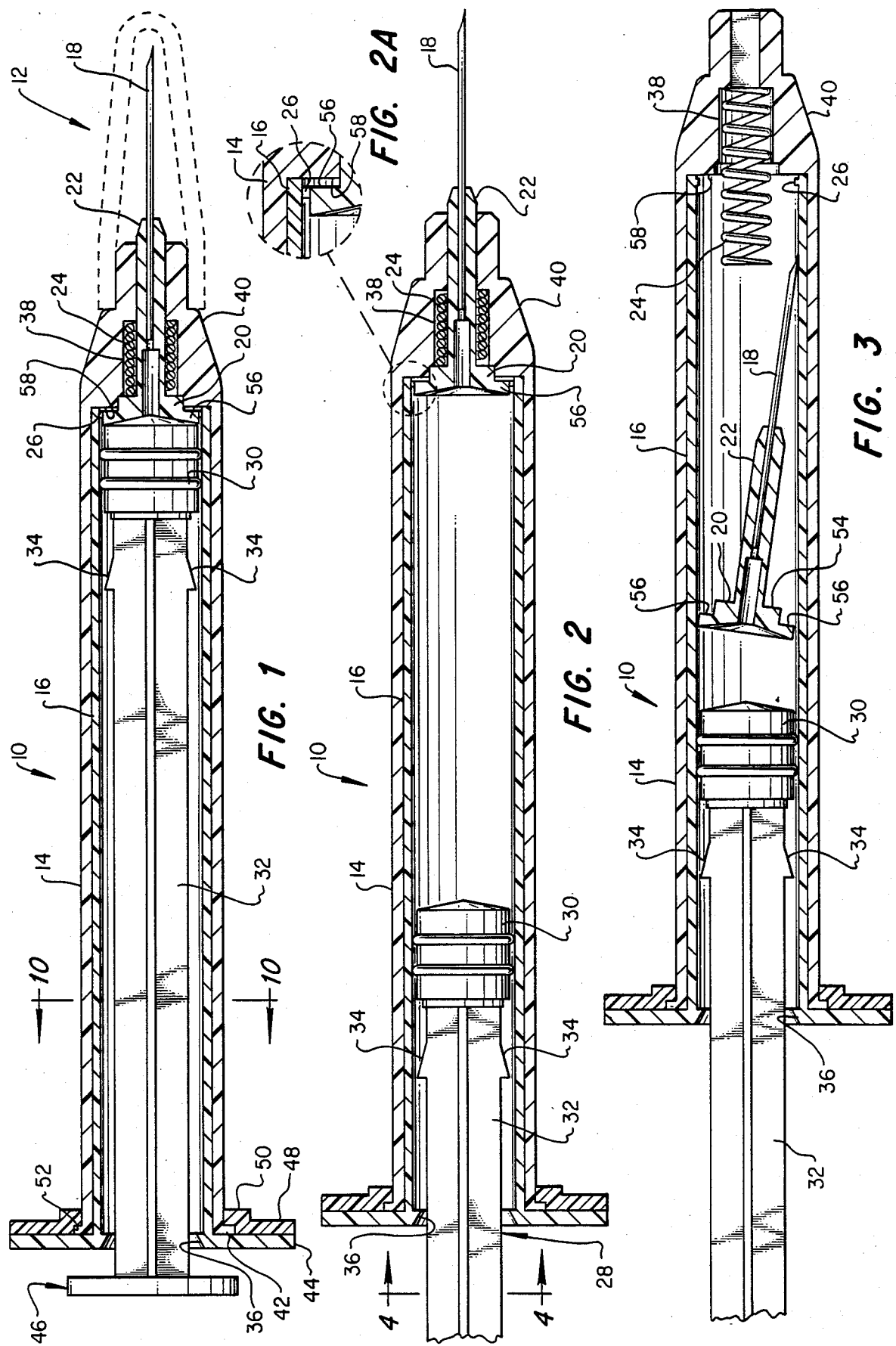

DISPOSABLE SYRINGE WITH RETRACTING NEEDLE

FIELD OF INVENTION

The present invention generally relates to hypodermic syringes and more particularly relates to a disposable hypodermic syringe which is readily disabled after its intended use against re-use and also against the dangers of needle sticking during subsequent handling and disposal.

BACKGROUND OF THE INVENTION

The medical workers who use hypodermic syringes incur considerable possibility of receiving sticks or pricks from the hypodermic needles used in the course of their daily work. Workers who clean up the medical facilities also incur the possibility of such needle pricks. Communicable diseases such as hepatitis and AIDS can be transmitted by these needle pricks. The need is evident for a hypodermic syringe which is disposable and which is readily disabled against the possibility of needle pricks and also against re-use.

The hypodermic syringe of the present invention requires few component parts, including a removable protective cap, and each of the parts may be mass produced at relatively little expense.

The syringe of the present invention may be filled with liquid for injection into a subject in the same manner as the prior art syringes. After use, the syringe plunger may be retracted and the hypodermic needle released for retraction into the syringe chamber by holding the syringe barrel with one hand and the syringe holding flange with the other hand, then twisting or rotating the syringe flange with respect to the barrel member. The needle is released into the syringe reservoir by the torsion and is permanently contained within the reservoir. The syringe needle is disabled against accidental sticking.

The presently known prior art are U. S. Pat. Nos. 3,584,626; 4,542,749; 4,710,170; 4,747,830; 4,747,831; 4,767,413; 4,770,655; 4,790,822; and 4,795,432.

OBJECTS OF THE INVENTION

One object of the present invention is to provide a hypodermic syringe which can be permanently disabled against a needle stick or prick after its intended use.

Another object of the present invention is to provide a hypodermic syringe which is disposable after use.

A further object of the present invention is to provide a hypodermic syringe having component parts which are easily and economically molded by injection molding.

SUMMARY OF THE INVENTION

The foregoing and other objects and advantages of the present invention are provided in hypodermic syringe apparatus having a completely retractable needle. The syringe includes a hollow barrel member formed with a needle support opening at a first end and a reservoir body formed with a needle support carrier means at a first end. The reservoir body is retained against longitudinal movement while permitting rotational movement of the reservoir body within the barrel member. The needle support carrier means is retained against rotational movement while permitting longitudinal movement of the needle support carrier means within the needle support opening.

An elastic member is mounted in stressed relation between the needle support opening and the needle support carrier means for urging the needle support member to move into the reservoir body. A disconnectable connection means connects the needle support carrier means to the reservoir body and is adapted to be disconnected by rotational force applied between the barrel member and the reservoir body means. The elastic member is adapted to force the needle carrier means and the needle into the reservoir body when the connection means is disconnected. A liquid plunger means is mounted within the reservoir body for sucking liquid through the needle into the reservoir body and discharging liquid through the needle out of the reservoir body. The plunger member is retained within the reservoir body by at least one barb retainer means formed on the plunger member.

The reservoir body is retained within the barrel member by a keeper flange which keeps a flange on the reservoir body in contact with the other end of the barrel member. The needle carrier comprises a needle support post fitted in sliding and non-rotating relation within the needle support opening.

DESCRIPTION OF THE DRAWING

FIG. 1 is a partly schematic longitudinal cross-sectional view showing a hypodermic syringe including a protective cap as being ready for intended use;

FIG. 2 is the same sectional view as FIG. 1 and showing the syringe plunger in a retracted position as when the reservoir body chamber has been filled with a liquid and/or when the plunger has been retracted to disconnect the reservoir body from the needle carrier member;

FIG. 2A is an enlarged view taken from FIG. 2 and showing in more detail the partable web link which connects the reservoir body with the needle carrier member;

FIG. 3 is similar to FIGS. 1 and 2 and shows the needle carrier member and needle permanently moved into and retained within the reservoir body chamber;

DESCRIPTION OF THE PREFERRED EMBODIMENT

FIGS. 1, 2, 2A, and 3 show the hypodermic syringe 10 as provided by the present invention. In FIG. 1, the syringe 10 is seen to include a removable protective cap 12.

Figure 8:
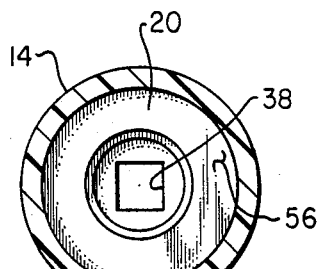
FIG. 8 is a partly sectional and partly elevational view of the syringe barrel as shown at line 8—8 in FIG. 5.
Figure 9:
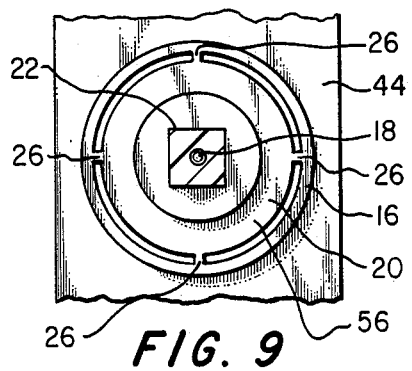
FIG. 9 is a partly sectional and partly elevational view of the reservoir body as taken along the line 9—9 of FIG. 6.

As seen in FIG. 1, the outer barrel member 14 is formed with a barrel retainer flange 42 and a needle support opening 38 which is formed by a needle support collar 40. The support collar 40 forms a support shoulder 58 and two counterbores; the smaller counterbore houses a spring 24. Part of the opening 38 is square in configuration as shown in FIG. 8. Fitted within the barrel member 14 is an inner reservoir body 16 which is attached to a needle support member 20. Support member 20 carries a needle support post 22 and a radially disposed support flange 56. The support flange 56 is connected to the end of the reservoir member 16 by means of a plurality of webs or links 26 as best shown in FIG. 2A and FIG. 9.

The reservoir body 16 is formed with a reservoir flange 44 at the other end. The inner bore of the flange 44 is formed with a ramp 36 for use as later described.

Figure 10:
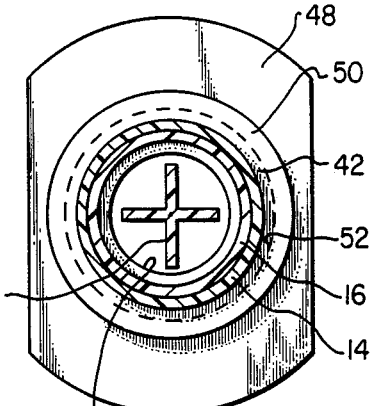
FIG. 10 is a partly sectional and partly elevational view of the assembled hypodermic syringe as shown at from line 10—10 of FIG. 1.

In view of FIG. 1 and FIG. 10, the reservoir flange 44 and the barrel retainer flange 42 are seen to be retained in contiguous position by means of a keeper flange 48. As shown, the keeper flange 48 has a keeper retainer recess 52 which contains the barrel retainer flange 42. The recess 52 may be formed in connection with a boss 50 in an injection molding operation. The keeper flange 48 is connected to the reservoir flange 44 by means of ultrasonic welding, as a preferred fastening means. As shown in FIG. 1, the flanges 44 and 48 are free to rotate about the barrel retainer flange 42 while at the same time restraining the longitudinal movement of the reservoir body 16 within the barrel member 14.

FIG. 10 shows a plunger shaft 32, the body member 16, and the barrel 14 in cross-section. The ramp 36, the keeper retainer recess 52, and the barrel retainer flange 42 are indicated by a dashed line. The boss 50 is shown with respect to the keeper flange 48.

Referring now to FIG. 2, the syringe 10 is shown with the plunger member 28 in position withdrawn out of the reservoir body 16 indicating that the reservoir formed by the reservoir 16 has been filled with a liquid medication of some designation. Also, the plunger member 28 is placed in this position in order to provide space for the needle support member 20 and its hypodermic needle 18 to be stored within the reservoir body 16 after being separated from the body member 16.

Figure 4:
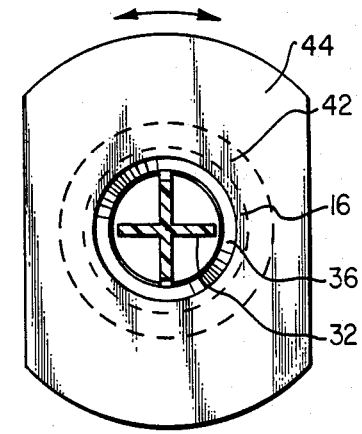
FIG. 4 is a partly sectional and partly elevational view taken at line 4—4 of FIG. 2.

FIG. 4, taken at 4—4 of FIG. 2, shows the reservoir flange 44, the ramp 36, and the plunger shaft 32.

FIG. 2A is an enlarged detail showing the barrel member 14, the reservoir body 16, the web support flange 56, and the web link 26 connecting the flange 56 to the reservoir body 16. In FIG. 2, the spring 24 is shown as being in compression between the needle support member 20 and the counterbore in collar 40, and the spring is held in compression by a plurality of the web links 26 as shown in FIG. 2A and FIG. 9.

FIG. 3 shows the syringe 10 with the needle support member 20 separated from the reservoir body 16 wherein the spring 24 has forced the needle support member 20 and its hypodermic needle 18 into the chamber within reservoir body 16. It is to be noted that spring 24 could be provided of a tubular elastomer such as rubber.

Figure 5:
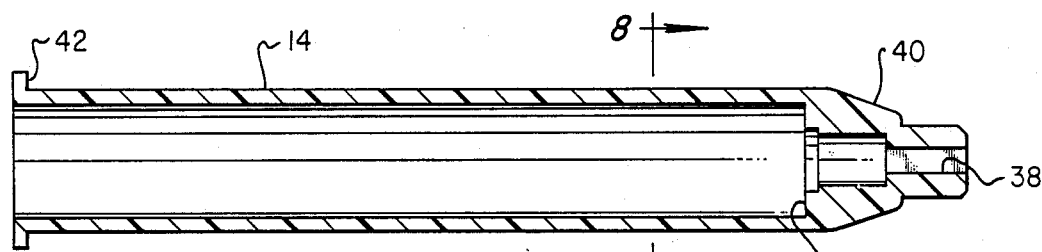
FIG. 5 is a longitudinal cross-sectional view of the syringe barrel member as utilized in FIGS. 1-3.

Referring now to FIG. 5, the outer barrel member 14 is shown in greater detail. Shown are the retainer flange 42, the collar 40, the opening 38, the support shoulder 58, the first counterbore, and the smaller counterbore which houses the spring 24.

FIG. 8 shows the barrel 14 in section, the shoulder 56, the counterbores, and the opening 38 in elevation. The opening 38 is shown as being square, but other spline arrangements such as spline teeth or other non-circular cross-sections could be utilized. In such event, the needle support post 22, as shown in FIGS. 1 and 2, would be of corresponding outside circumference so that the post 22 could reciprocate within the opening 38 but could not rotate within opening 38.

Figure 6:
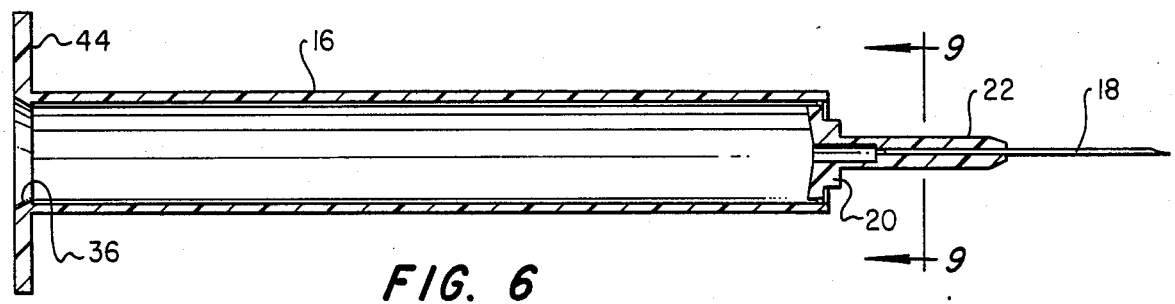
FIG. 6 is a longitudinal cross-sectional view of the reservoir body and the needle carrier member as utilized in FIGS. 1-3.

FIG. 6 and FIG. 9 show the reservoir body 16 to have the reservoir flange 44 and the ramp 36 at one end and the needle support member with the flange 56 and the web links 26 being shown in elevation. As shown, the web links 26 are symmetrically arranged around the circumference of the bulkhead 66 and within the inner wall of the reservoir member 16. The rotation, or torque urging rotation, of the reservoir body 16 within the barrel member 14 places stress on the web links 26 until, at some designated torque, the web links 26 are sheared or parted, leaving the flange 56 free to move longitudinally with respect to the reservoir body 16. As shown with respect to FIGS. 2 and 3, the support member 20 is urged into the chamber of reservoir body 16 by the forceful expansion of the spring 24. This movement is rather rapid, and the support member 20 attains some inertia which carries it up against the plunger piston 30 before it comes to rest as shown in FIG. 3. The needle 18 is free of the spring 24.

Figure 7:
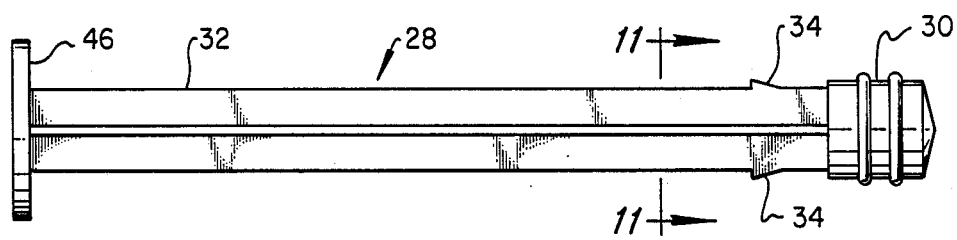
FIG. 7 is a longitudinal elevational view of the syringe plunger including its plunger piston and actuation flange.
Figure 11:
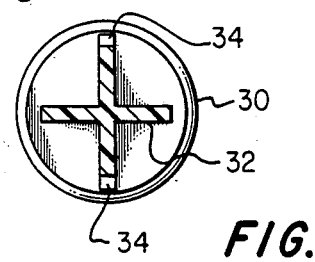
FIG. 11 is a partly sectional and partly elevational view of the syringe plunger as taken along the line 11—11 of FIG. 7.

FIG. 7 and FIG. 11 show the plunger member 28 in detail. As shown, the plunger member 28 is formed with a flange 46 at one end and a plunger piston 30 is attached at the other end. The plunger member 28 is equipped with barbed retainer means 34 which have been formed to retain the plunger 28 within the reservoir body 16. When the plunger 28 is brought into the reservoir body 16, the piston 30 and the barbs 34 are forced past the ramp 36 responsive to some distortion between the plastic members. After the plunger 28 has been pushed into the reservoir body 16, the barbs 34 prevent removal of the plunger 28 because the ramp 36 forms a buttress beyond which the barbs 34 may not pass.

In operation, the syringe 10 is assembled as shown in FIG. 1 in readiness for its intended use. When used, the protective cap 12 is first removed, and the plunger piston 30 is withdrawn as shown in FIG. 2, usually to suck some liquid medication through needle 18 into the reservoir or chamber formed within the barrel member 16. The syringe 10 is used as any other syringe is used, and after its use has been completed, the plunger is withdrawn to a position as shown in FIG. 2. To disable the syringe against further use and to pull the needle out of any anti-stick position, the barrel member 14 is held with one hand and the composite flange 44-48 is gripped by the other hand. With this grip as described, torque is applied to the reservoir body 26 with respect to the needle support member 20. A shearing force is applied by such torque to the web links 26. At some designated torque force, which is within the capability of a very small person, the web links 26 are parted or broken due to the shearing action between the body 16 and the support member 20.

When the web links 26 are parted, the spring 24 then forcefully urges the support member 20 away from the shoulder 58 until the entire support member 20 and needle 18 are completely confined within the reservoir body 16.

It is to be noted that the relative dimensions of the spring 24, when fully expanded, are sufficiently long in order to push the entire support member 20 and hypodermic needle 18 positively to within the reservoir body 16.

If desired, a portion of the plunger 32 of the plunger member 38 can be serrated to facilitate being broken and removed as shown in some of the prior art. This would be an optional feature not shown in the present drawings.

It will be apparent to those skilled in the art that modifications and changes may be made to the embodiment as shown and described without departing from the spirit or scope of the invention which is set forth in the appended claims.

What Is Claimed:

1. Hypodermic syringe apparatus having a completely retractable needle comprising, in combination:
    (a) a hollow barrel formed with a needle support opening at a first end;
    (b) a reservoir body formed with a needle support carrier at a first end;
    (c) said reservoir body being retained against longitudinal movement within said barrel member while permitting rotational movement of said reservoir body within said barrel member;
    (d) said needle support carrier being retained against rotational movement within said barrel member while permitting longitudinal movement of said needle support carrier within said needle support opening;
    (e) an elastic member mounted in stressed relation between said needle support opening and said needle support carrier for urging said needle support member out of said needle support opening into said reservoir body;
    (f) disconnectable connection means connecting said needle support carrier to said reservoir body disconnection by torque applied between said barrel member and said reservoir body;
    (g) said elastic member forcing said needle carrier and said needle into said reservoir body when said connection means is disconnected; and
    (h) a liquid plunger mounted within said reservoir body for sucking liquid through said needle into said reservoir body and discharging liquid through said needle out of said reservoir body.

2. The apparatus of claim 1 wherein said connection means comprises at least one separatable link radially connecting said reservoir body with said needle carrier.

3. The apparatus of claim 1 wherein said elastic member comprises a coil spring mounted in compression.

4. The apparatus of claim 1 wherein said elastic member comprises an elastomeric member mounted in compression.

5. The syringe of claim 1 wherein said reservoir body is retained within said barrel member by a retainer flange confined between a reservoir body flange and a keeper flange fastened to said reservoir body flange.

6. The syringe of claim 1 wherein said needle carrier comprises a needle support post fitted in sliding and non-rotating relation within said needle support opening.

7. The apparatus of claim 1 wherein said plunger member is retained within said reservoir body by at least one barb retainer latch means.

8. The apparatus of claim 2 wherein said elastic member comprises a coil spring mounted in compression.

9. The syringe of claim 8 wherein said reservoir body is retained within said barrel member by a retainer flange confined between a reservoir body flange and a keeper flange fastened to said reservoir body flange.

10. The syringe of claim 9 wherein said needle carrier comprises a needle support post fitted in sliding and non-rotating relation within said needle support opening.

11. An anti-contagion hypodermic syringe apparatus adapted to be easily disabled against re-use or flesh pricking, comprising in combination:
    (a) (1) an outer barrel member, (2) an inner reservoir body fitted within said barrel member, (3) a needle support member removably connected to said reservoir body, (4) a hypodermic needle mounted in said support member for extension out of said barrel member, (5) an elastic member mounted in stressed condition between said needle support member and said barrel member for moving said needle into said barrel member when said elastic member is released from stressed condition, and (6) a plunger member including a plunger piston fitted in reciprocative relation within said reservoir body for sucking and ejecting liquid through said needle;
    (b) said needle support member being mounted for permitting its longitudinal movement within said barrel member while preventing its rotational movement within said barrel member;
    (c) said barrel support member being connected to said reservoir body through disconnect linkage which is partable when stressed; and
    (d) said reservoir body being rotatably mounted within said barrel member with construction and arrangement for parting said disconnect linkage responsive to a designated torque applied between said barrel member and said reservoir body with said needle support member becoming free for relieving said stress on said elastic member with said elastic member thereby moving said needle support member and said needle to within said reservoir body chamber.

12. The apparatus of claim 11 wherein said disconnect linkage comprises a partable link radially connecting said support member in concentric relation with one end of said reservoir body.

13. The syringe of claim 11 wherein said elastic member comprises a coil spring mounted in compressed condition.

14. The syringe of claim 11 wherein said elastic member comprises an elastomeric member mounted in compression.

15. The syringe of claim 11 wherein said reservoir body is retained within said barrel member by a retainer flange formed at one end of said barrel member and confined between a reservoir body flange connected to a keeper flange with the retainer flange in between.

16. The syringe of claim 11 wherein said needle support member includes a needle support post fitted in sliding and non-rotating relation through an aperture formed in the distal end of said barrel member.

17. The syringe of claim 16 wherein said plunger member is retained within said reservoir body by at least one barb retainer means formed by said plunger member and expanded into place behind an abutment means formed at one end of said reservoir body.

18. Hypodermic syringe apparatus having a retractable needle comprising, in combination:
   (a) a hollow barrel formed with a needle support opening at a first end;
   (b) a reservoir body formed with a needle support carrier at a first end;
   (c) said reservoir body being retained against longitudinal movement within said barrel member while permitting rotational movement of said reservoir body within said barrel member;
   (d) said needle support carrier being retained against rotational movement within said barrel member while permitting longitudinal movement of said needle support carrier within said needle support opening;
   (e) an elastic member mounted in stressed relation between said needle support opening and said needle support carrier for urging said needle support member to move out of said needle support opening into said reservoir body;
   (f) disconnectable linkage means connecting said needle support carrier to said reservoir body for disconnection by rotational force applied between said barrel member and said reservoir body; and
   (g) said elastic member forcing said needle carrier and said needle into said reservoir body when said connection means is disconnected.

19. The apparatus of claim 18 wherein said linkage means comprises at least two separatable links radially connecting said reservoir body with said needle carrier means.

20. The apparatus of claim 18 wherein said elastic member comprises a coil spring mounted in compression.

* * * * *